United States Patent
Vigolo (10) Patent No.: US 7,306,457 B2
(45) Date of Patent: Dec. 11, 2007

(54) SELF-LIGATING ORTHODONTIC PASSIVE LOW-FRICTION BRACKET AND METHOD FOR MOUNTING AN ARCH WIRE ON SAID BRACKET

(76) Inventor: Valter Vigolo, Via Roma, 67, I-35036, Montegrotto (IT)

( * ) Notice: Subject to any disclaimer, the term of this patent is extended or adjusted under 35 U.S.C. 154(b) by 0 days.

(21) Appl. No.: 11/402,276

(22) Filed: Apr. 12, 2006

(65) Prior Publication Data

US 2006/0246392 A1 Nov. 2, 2006

Related U.S. Application Data

(63) Continuation-in-part of application No. PCT/IT2004/000635, filed on Nov. 16, 2004.

(30) Foreign Application Priority Data

Nov. 20, 2003 (IT) .......................... PD2003A0278

(51) Int. Cl.
*A61C 3/00* (2006.01)
(52) U.S. Cl. .................. 433/10; 433/8; 433/9; 433/11; 433/12
(58) Field of Classification Search .................. 433/10, 433/8, 9, 11, 12
See application file for complete search history.

(56) References Cited

U.S. PATENT DOCUMENTS

| | | | | |
|---|---|---|---|---|
| 2,104,192 A | * | 1/1938 | Ford | 433/10 |
| 2,926,422 A | * | 3/1960 | Wallshein | 433/8 |
| 3,765,091 A | | 10/1973 | Northcutt | |
| 4,037,324 A | * | 7/1977 | Andreasen | 433/24 |
| 4,529,382 A | * | 7/1985 | Creekmore | 433/9 |
| 4,664,626 A | * | 5/1987 | Kesling | 433/16 |
| 4,859,179 A | * | 8/1989 | Kesling | 433/8 |
| 5,125,832 A | * | 6/1992 | Kesling | 433/8 |
| 5,470,228 A | * | 11/1995 | Franseen et al. | 433/8 |
| 5,616,026 A | | 4/1997 | Cash | |
| 6,682,345 B2 | * | 1/2004 | Kesling et al. | 433/8 |
| 2002/0197581 A1 | * | 12/2002 | Georgakis et al. | 433/10 |
| 2003/0180678 A1 | | 9/2003 | Kesling et al. | |

FOREIGN PATENT DOCUMENTS

WO   WO 03/045266 A1   6/2003

\* cited by examiner

*Primary Examiner*—Melba N. Bumgarner
*Assistant Examiner*—Jonathan Werner
(74) *Attorney, Agent, or Firm*—Browdy and Neimark, PLLC (57) ABSTRACT

Self-ligating orthodontic bracket which comprises a support body (6) intended to be fixed onto a tooth and provided with a slot (9) for receiving an arch wire (5) capable of imparting a corrective action to the tooth and retaining means (10) able to interfere with the wire (5) so as to lock it inside the slot (9) The retaining means (10) are formed by a pair of lugs (10') made as one piece with the support body (6) and having a retaining portion (11) which delimits the slot (9) at the top and interferes with the wire (5). The said lugs (10') are provided with two opposite faces which delimit an opening (21) of a channel (20) for access to the slot (9).

11 Claims, 6 Drawing Sheets

SELF-LIGATING ORTHODONTIC PASSIVE LOW-FRICTION BRACKET AND METHOD FOR MOUNTING AN ARCH WIRE ON SAID BRACKET

The present invention concerns a self-ligating orthodontic bracket of the passive low-friction type and a method for mounting an arch wire on the said orthodontic bracket.

The invention in question relates to the sector of dental orthodontics or that branch of dentistry which deals the prevention and treatment of malocclusions.

In order to treat malocclusions, traditionally fixed orthodontic apparatus and movable orthodontic apparatus are used, said apparatus being selected depending on the specific aim of the treatment.

In particular, in the case of fixed orthodontic treatment, correction of the incorrectly aligned teeth is performed using apparatus which are glued or cemented to the teeth for the whole duration of the treatment. The fixed apparatus allows displacement of the teeth also by large amounts, in all directions and with any type of movement, including body movement, such that its use allows the correction of incorrectly positioned teeth which cannot be treated using other apparatus.

A fixed orthodontic apparatus traditionally comprises a plurality of metal or ceramic fixtures which are commonly known by the term bracket and which form the parts intended to be fixed to the teeth for the duration of the treatment and at least one metal band or wire which is fastened to the brackets so as to impart to the teeth a displacement intended to bring them into the correct position.

As is known, dental orthodontics which employs fixed orthodontic apparatus has developed, within its own area, different techniques which vary from each other mainly in terms of the position assumed by the apparatus inside the mouth, which may be vestibular or lingual, or in terms of the bracket used, which may be for example of the straight wire type—which is at present the most used and whereby displacement of the teeth is determined, by the shape of the slot—or of the tweed type—in which displacement of the teeth is determined mainly by the form and the arrangement of the wire.

By means of the form of the slot (straight wire technique) or the arrangement of the wire (tweed technique) three-dimensional control and varying movement in the position of the teeth is obtained. In other words, it is possible to use different movements in order to achieve the various occlusions, including primarily and most commonly, mesio-distal tipping or angling of the crowns, labio-lingual or vestibulo-lingual torque or inclination of the crowns, or rotation and inward/outward movement of the latter in order to define respectively the correct orientation and the correct position of the teeth in the upper and lower dental arch.

Generally speaking, irrespective of the type of technique used, a very widespread embodiment of a bracket, shown schematically in Figure A, comprises a base B with a treated contact surface allowing adhesion to the tooth, a support body C provided with a seat D having a generally rectangular cross-section, known in the technical jargon of the sector, by the term "slot", for insertion of a band in the form of a metal wire, and two or more lugs E for retaining ligatures necessary for fixing the wire (not shown) inside the slot.

The ligatures used at present may be of the elastic or metallic type, and act on the wire by means of friction.

In greater detail, elastic ligatures are prone to easy deterioration and exert a frictional force on the wire which limits the speed of movement thereof.

Metallic ligatures, which are practically not subject to any wear, exert, however, a frictional force on the wire and may interfere with the mucus membranes of the mouth, causing wounds.

The use of conventional brackets with friction ligatures, both of the elastic and of the metallic type, in practice has therefore proved to have certain drawbacks.

A drawback consists in the fact that the ligatures both of the elastic type and of the metallic type are difficult to fit inside the patient's mouth such that sessions which are very long and uncomfortable for the patient are required.

Obviously this aspect has a notable negative effect on the productive efficiency of the orthodontist.

Another drawback consists in the ligatures of the elastic type which have mechanical characteristics which deteriorate fairly rapidly, in particular when a limit tension value is exceeded, beyond which value these ligatures are no longer able to retain the wire inside the slot.

The ligatures of the metallic type, although withstanding higher tensile forces than the ligatures of the elastic type, do not exert a constant compressive action on the wire and therefore require continuous adjustment upon variation in the position of the tooth.

In order to overcome the drawbacks encountered in brackets of the known type described above and associated mainly with the limited ease of fixing the wires together with all the resultant problems for the patient and the efficiency of the orthodontist, more recently designs of self-ligating brackets mainly of two types, i.e. an active type and passive type, have been developed.

In active self-ligating brackets a tongue closes and pushes the wire into the slot, causing friction as a result of attrition.

In passive self-ligating systems a tongue closes the wire inside the slot without exerting substantially any pressure on the wire, thereby producing a low-friction system with low attrition. Both the bracket designs envisage, however, the use of a retaining element which is movable slidably or rotatably on the support body between a closed position, where this movable element retains the wire inside the slot, and an open position, where this movable element does not interfere with the wire, freeing the slot.

More particularly, the patents U.S. Pat. Nos. 6,071,119, 5,906,486 and 5,586,882 describe the use of a bracket shown schematically in Figure B and comprising a retaining element F which is provided with a first portion F1 arranged slidably inside a guide formed on the support body and a second portion F2 able to be arranged so as to close and open the slot and connected continuously to the first portion by means of a U-shaped intermediate portion F3.

In accordance with this solution, the opening action is performed by acting on a free end G of the first portion F1 and the closing action is performed by acting on the intermediate connecting portion F3.

The solutions of the known type mentioned above, with a movable retaining element F, although resulting in a shorter fitting time for the brackets, have proved to be somewhat complex and difficult to realize from a constructional point of view.

Moreover, the said retaining element F thus formed has a mechanical strength which is not entirely satisfactory and is therefore prone to breakages.

The difficulties associated with closing and opening of this element F therefore do not allow very easy and rapid use of the bracket.

As is known, moreover, wires of the form-memorizing superelastic type (for example nickel-titanium) are preferred during some stages of treatment of the malocclusions compared to rigid steel wires.

As is known, form-memorizing superelastic wires are generally used during the first stages of treatment and may have the same cross-sections as steel wires. The latter are known on the market as being more rigid than superelastic wires and are generally used during the final stages of treatment.

The problem underlying the present invention is therefore that of overcoming the drawbacks of solutions of the known type described above by providing a self-ligating, passive, low-friction orthodontic bracket which allows a reduction in the time required for engagement of the superelastic wire and can be used in a versatile manner both with steel wires and with superelastic wires.

A further object of the present invention is that of providing a bracket which is constructionally inexpensive to produce, easy to fit and operationally entirely reliable.

A further object of the present invention is that of providing a method for mounting an arch wire on a self-ligating orthodontic bracket which can be performed in a simple and rapid manner.

The technical features of the invention, in accordance with the abovementioned objects, may be determined from the claims provided below and the advantages thereof will emerge clearly from the detailed description which follows, with reference to the accompanying drawings which illustrate some purely exemplary and non-limiting examples of embodiment in which:

In accordance with the figures of the accompanying drawings, 1 denotes in its entirety the self-ligating orthodontic bracket forming the subject of the present invention.

The orthodontic bracket 1 in question is intended to be used in a fixed apparatus for correcting misalignment of the upper and lower dental arches.

By applying the usual modifications known to a person skilled in the art, it may be adapted equally well for use both in the technique using vestibular apparatus and in the technique using lingual apparatus. Moreover, it is possible to adopt any orthodontic technique on all the teeth of the dental arch—including the molars—whether it be for example of the straight-wire type or also, to a more limited degree, of the tweed type, without departing as a result from the scope of protection of the present patent.

Figure 1:
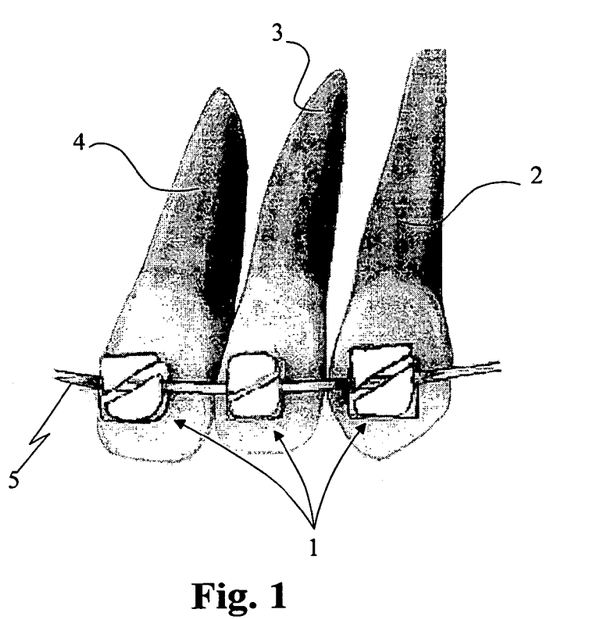
FIG. 1 shows schematically an overall perspective view of a fixed orthodontic apparatus mounted on three teeth and provided with three corresponding brackets according to the invention.

FIG. 1 shows, purely by way of example, a portion of an apparatus associated with three teeth, i.e. a canine tooth 2, a lateral incisor 3 and a central incisor 4, on which three corresponding orthodontic brackets 1 according to the present invention are mounted and joined together by means of an arch wire 5.

Figures show some embodiments of a self-ligating orthodontic bracket 1 according to the invention in an entirely schematic form, it being understood that the forms and surfaces may vary, taking into account in particular, in a manner known per se, the interaction with the gums and the tongue or the need to provide button or hooks for the engagement of elastic elements, springs or other devices of a type known per se, Also the material from which the bracket 1 is made does not form the subject of a specific claim and therefore the bracket may be made equally well ox metal (steel), using the technique known as "metal injection moulding", or ceramics, using the technique known as "ceramic injection moulding" or also polycarbonate and steel for reasons usually of an aesthetic nature.

The self-ligating orthodontic bracket traditionally comprises a support body 6 provided with a base 7 having a contact surface intended to be fixed onto a tooth. This surface is preferably suitably treated for optimum retention on the tooth and, depending on requirements, may have a shape which is flat or curved in accordance with the profile of the tooth. It may also be fixed by direct mounting using glues or cements or may be attached to orthodontic bands.

Figure 2:
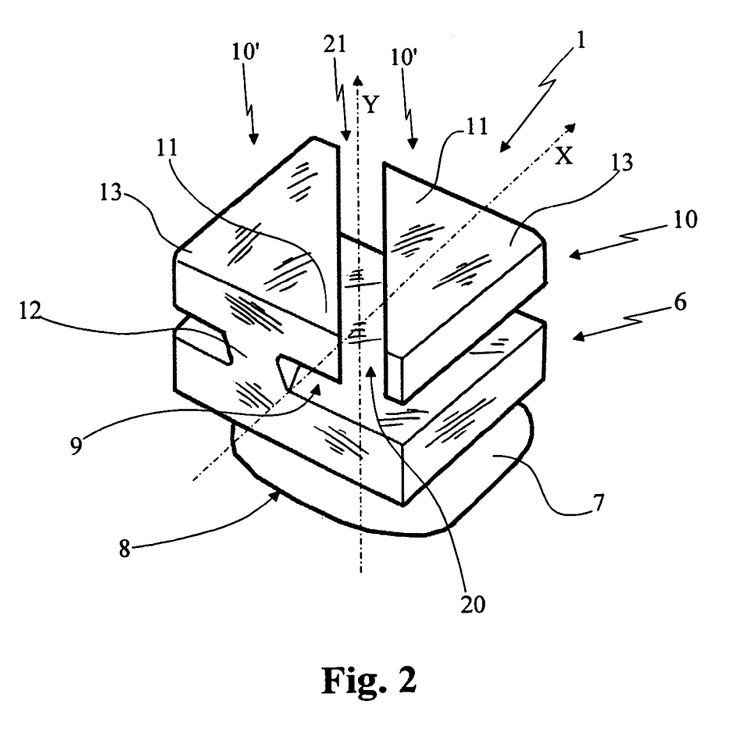
FIG. 2 shows a perspective view of a first embodiment of an orthodontic bracket according to the invention.
Figure 3:
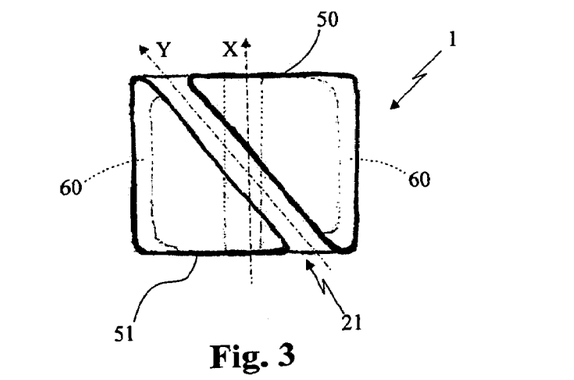
FIG. 3 shows a top plan view of the bracket according to FIG. 2.

With particular reference to FIG. 2 the support body 6 has, passing through it, a seat which in the technical jargon of the sector is known by the term "slot". Said slot, which is denoted by 9 in the figures, extends substantially in a receiving direction X and is able to receive inside it the arch wire 5. The action of the latter on the slot 9 allows the three-dimensional control and varied movement of the position of the tooth.

According to the present invention retaining means 10 are envisaged for fixing the wire inside the slot 9, said means comprising at least one lug 10'. The latter forms one piece with the support body 6 and delimits partially the slot 9 by means of a retaining portion 11 so that the lug 10 interferes with the wire 5 at least along a direction of engagement. The said lug 10' also defines an access channel 20 which is constantly in communication with the slot 9.

In accordance with a preferred embodiment of the present invention, two separate lugs 10' are envisaged, said lugs having a substantially mushroom shape with shanks 12 extending in a projecting manner from the support body 6 and with head pieces 13 joined integrally to the respective shanks 12 and provided with two opposite surfaces 14 which define an opening 21 which extends mainly in a longitudinal direction Y and helps define the access channel 20.

Figure 4:
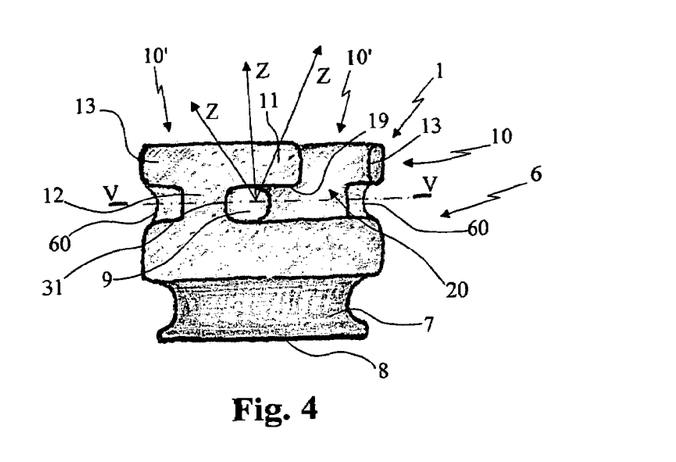
FIG. 4 shows a side view of the bracket according to FIG. 2.

Each head piece 13 extends above the slot 9 with the abovementioned retaining portion 11 by means of which it restrains the wire 5 inside the slot 9, preventing it from moving substantially in any engaging direction indicated by Z in FIG. 4 different from that directed towards the access channel 20.

Each retaining portion 11 has a prismatic extension which delimits the abovementioned slot 9 by means of a bearing surface 19 having a substantially triangular shape.

Figure 5:
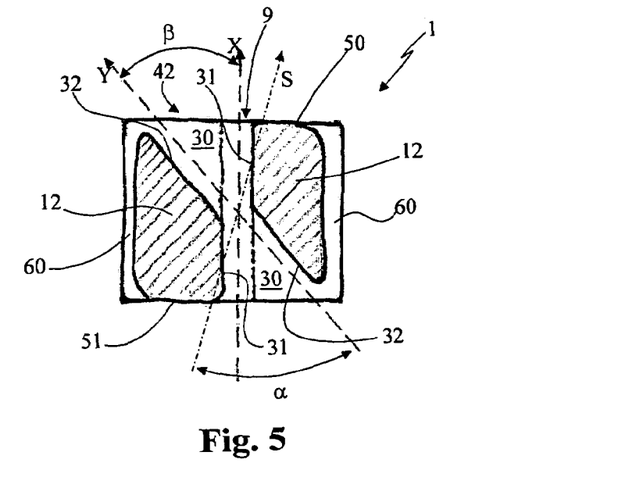
FIG. 5 shows a cross-sectional view along the line V-V in FIG. 4.

In greater detail, as can be seen in FIG. 5, the slot 9 and the access channel 20 define together a widened seat delimited at the bottom by a support surface 30 provided on the support body 6, laterally by two first sides 31 of the shanks 12 arranged so as to delimit the slot 9 and by two second sides 32 of the said shanks 12 arranged so as to delimit the access channel 20, and at the top by the abovementioned bearing surfaces 19.

The abovementioned support surface 30 is composed of two widened zones provided on two opposite sides 50, 51 of the bracket 1, one for receiving and the other for guiding out the wire 5, said zones gradually tapering in a linear manner so as to define substantially two triangles towards a central zone arranged so as to connect the two widened zones. In the abovementioned central zone, the slot 9 does not grip the wire 5.

Operatively speaking, the interaction of the wire 5 with the slot 9 produces a corrective thrusting action on the tooth until a final position of the tooth is reached, corresponding to an optimum arrangement of the wire 5 where the latter is substantially no longer active on the slot 9.

The access channel 20 is formed with an opening 21 oriented so that the receiving direction X of the slot 9 defines together with the longitudinal axis Y of the opening 21 itself an acute angle $\beta$ preferably between 5 and 50°.

So that the wire 5 is able to interfere with the slot 9 so as to allow for example mesio-distal displacement of the tooth, it is necessary for the receiving direction X of the slot 9 to be initially contained within the angle $\alpha$ subtended between the longitudinal axis Y of the opening 21 and a corrective direction indicated by S in FIG. 5 and theoretically assumed by the slot 9 following displacement of the tooth, i.e. when the two directions X and S coincide.

Advantageously grooves 60 may be provided for insertion, where necessary, of ligatures of the conventional elastic or metallic type.

The wires may consist, for example, of steel or a wire made of nickel/titanium, nickel/titanium/copper or other material and may be formed as a single wire or several interwoven wires, may be designed with a finish and external form which vary depending on the specific applicational requirements, for example, the cross-section may consist of a full cross-section in relation to the slot and for example be square, rectangular, circular or D-shaped and may have so-called "superelastic" or elastic properties or an elasticity depending on the temperature or may also be substantially rigid and may be employed both twisted and untwisted.

The bracket design according to the present invention allows replacement of the type of wire used during treatment of malocclusions in an very easy manner, making it possible in particular to change from wires initially of the form-memorizing superelastic type to steel wires or more generally to wires with little or no form memory. Both types of wire may be easily replaced with wires ranging, for example, from wires with a round cross-section and with smaller dimensions than the slot to wires with increasingly larger cross-sections, up to full thickness dimensions in relation to the slot.

Figures 6, 8:
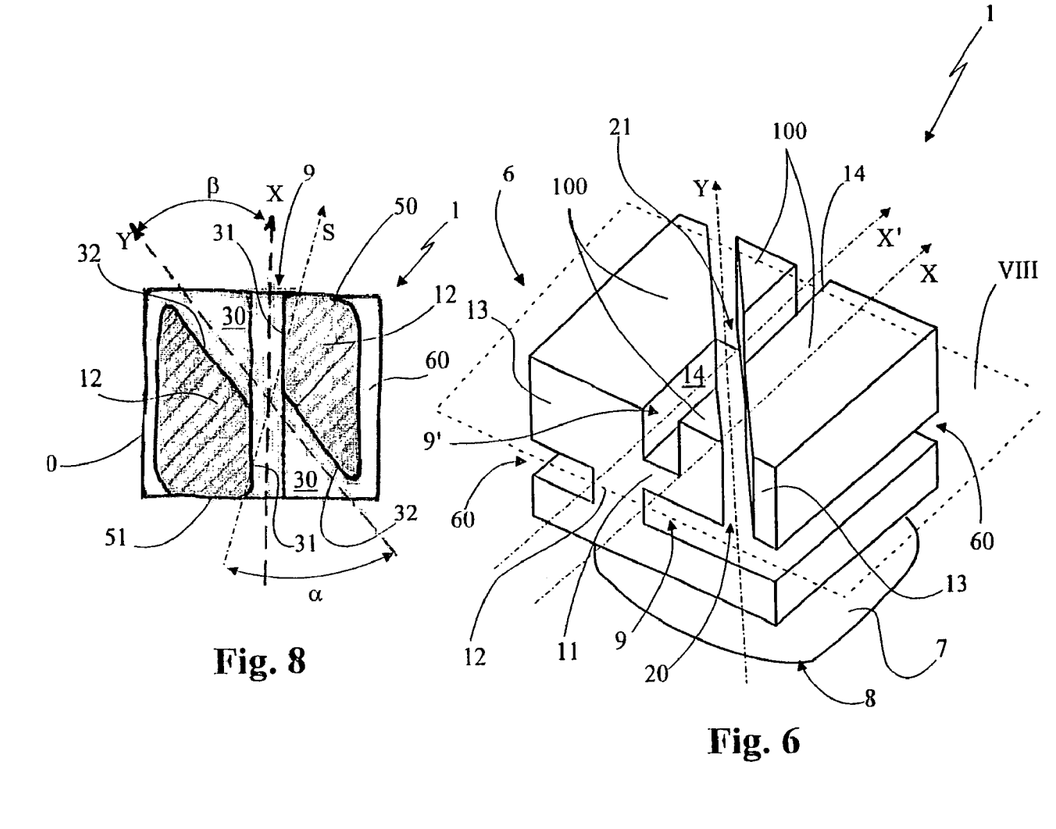
FIG. 6 shows a perspective view of a second embodiment of an orthodontic bracket according to the invention.
FIG. 8 shows a sectional view along the plane VIII of FIG. 6.
Figure 7:
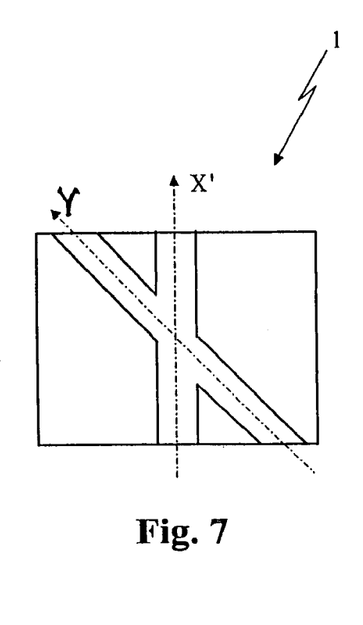
FIG. 7 shows a top plan view of the bracket according to FIG. 6.

With particular reference to FIG. 6, the support body 6 has, passing through it, a first and second seat indicated respectively by 9 and 9', which, in the technical jargon of the sector, are referred to by the term "slots", said seats extending in a first and second receiving direction X and X' and each being able to receive inside it an arch wire 5. The action of the latter on each slot 9, 9' allows the three-dimensional control and varied movement of the position of the tooth.

In greater detail, according to the embodiment of FIG. 6, the second slot 9' is formed so as to receive a wire, in particular made of steel, which is retained by means of conventional elastic ligatures able to impart an elastic force to the wire, or by means of metallic ligatures.

The slot 9' may have dimensions expressed in inches, for example 0.18 and 0.30 inches or 0.22×0.30 inches.

Figure 9:
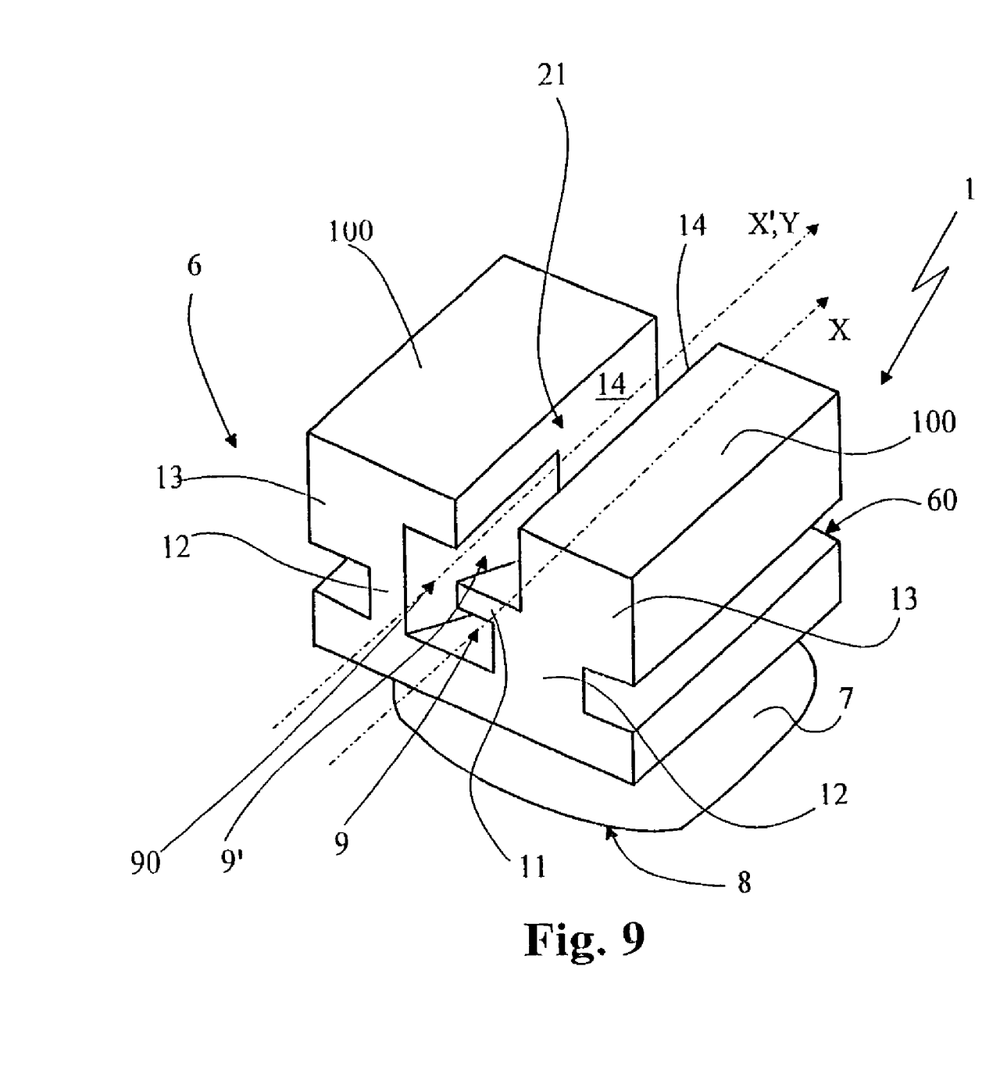
FIG. 9 shows a perspective view of a third embodiment of an orthodontic bracket according to the invention.
Figure 10:
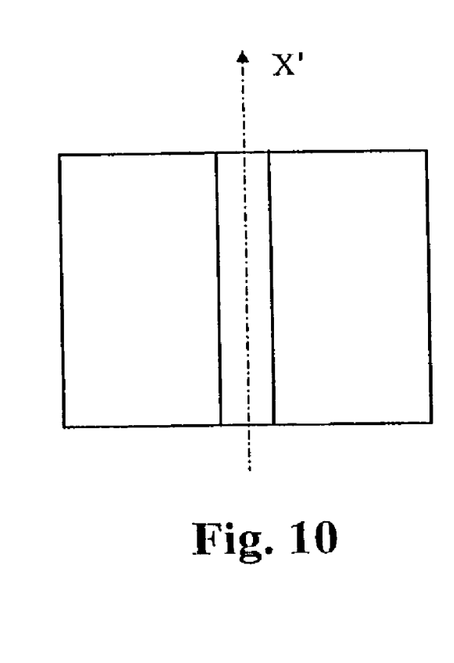
FIG. 10 shows a schematic plan view of the bracket according to FIG. 9.
Figure 11:
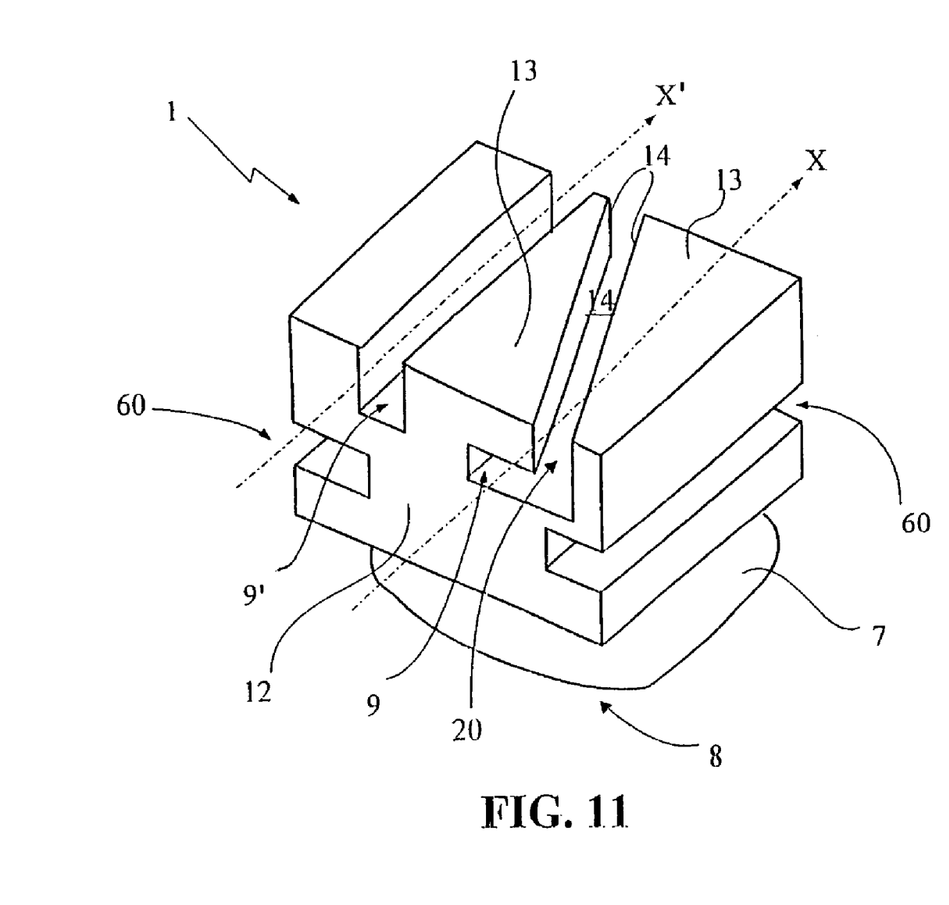
FIG. 11 shows a perspective view of a forth embodiment of an orthodontic bracket according to the invention.
Figure 12:
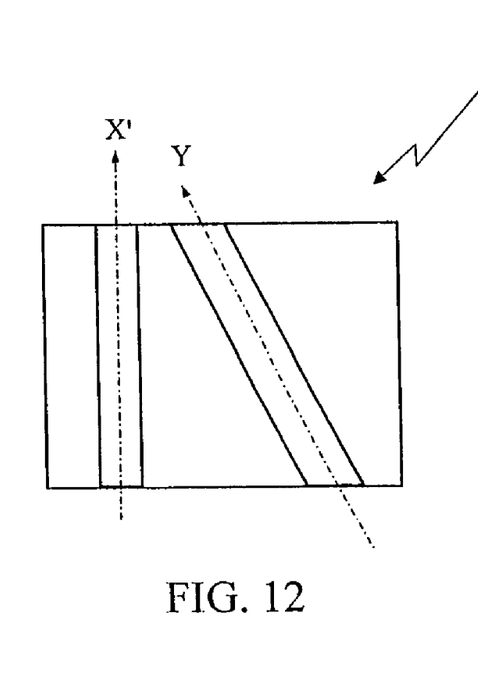
FIG. 12 shows a schematic plan view of the bracket according to FIG. 11.

Grooves 60 are envisaged, arranged laterally on the bracket, as shown in FIGS. 6, 9 and 11, so as to allow the provision of ligatures for retaining the wire 5, Differently, the first slot 9 is formed so as to allow insertion of a first wire, in particular a form-memorizing wire, which is retained by means of self-ligating fastening means described in detail below.

The form-memorizing superelastic wires may be easily deformed and therefore are particularly useful for use with the bracket 1 according to the present invention which requires easy insertion inside the second slot 9' by means of an access channel for the wire, having an orientation different from that of the slot.

In greater detail, the first slot 9 is associated with first retaining means 10 for fixing the wire inside it, said means comprising at least one lug 100 formed as one piece with the support 6.

The lug 100 also defines the access channel 20 which is constantly in communication with the slot 9 and has the function of allowing insertion of the wire 5.

In accordance with a preferred embodiment of the present invention, two separate lugs 100 are envisaged, said lugs having a substantially mushroom shape with shanks 12 extending in a projecting manner from the support body 6 and with head-pieces 13 joined integrally to the respective shanks 12 and provided with two opposite surfaces 14 which define an opening 21 of the access channel 20 oriented in a longitudinal direction Y of insertion of the wire 5.

Each head-piece 13 extends above the slot 9 with the abovementioned retaining portion 11 by means of which it restrains the wire 5 inside the slot 9, preventing it from moving substantially in any direction different from the direction of access of the channel 20.

In greater detail, as can be seen in FIG. 8, the slot 9 and the access channel 20 define together a widened seat delimited at the bottom by a support surface 30 provided on the support body 6, laterally by two first sides 31 and by two second sides 32 of the shanks 12 arranged so as to delimit the slot 9 and at the top by bearing surfaces 19 of the portions 11.

Each retaining portion 11 has a prismatic extension which delimits at the top the abovementioned slot 9 by means of the bearing surface 19 having a substantially triangular form.

The abovementioned support surface 30 is composed of two widened zones provided on two opposite sides 50, 51 of the bracket 1, one for receiving and the other for guiding out the wire 5, said zones gradually tapering in a linear manner so as to define substantially two triangles towards a central zone arranged so as to connect the two widened zones.

Operatively speaking, the interaction of the wire 5 with the slot 9 produces a corrective thrusting action on the tooth until a final position of the tooth is reached, corresponding to an optimum arrangement of the wire 5 where the latter is substantially no longer active on the slot 9.

The access channel 20 is formed with the upper opening 21 oriented along the longitudinal axis Y so that the receiving direction X of the slot 9 defines together with this axis Y an acute angle β preferably between 5 and 50°.

So that the wire 5 is able to interfere with the slot 9 so as to allow for example mesio-distal displacement of the tooth, it is necessary for the receiving direction X of the slot 9 to be initially contained within the angle α subtended between the longitudinal axis Y of the opening 21 and a corrective direction indicated by S in FIG. 8 and theoretically assumed by the slot 9 following displacement of the tooth, i.e. when the two directions X and S coincide.

As a result of the present invention it is therefore possible to perform with a single bracket a therapeutic treatment which envisages initially the use of wires of the-form-memorizing superelastic type to be seated inside the slot indicated by 9 and subsequently the use of steel wires in particular with a full thickness cross-section in relation to the slot, to be seated inside the slot indicated by 9'.

In accordance with the embodiment shown in FIG. 6, the access channel 20 for insertion of the superelastic wire intersects the second slot 9' transversely and thus allows access to the first slot 9 which is formed in the body 6 at a lower height than the first slot 9.

Differently, in accordance with the embodiment shown in FIG. 9, the access to the first slot 9 is achieved via an access channel which passes through the second slot 9' and envisages a section 90 connecting together the two slots 9, 9' which is preferably vertical such that the first slot 9 is situated lower than the second slot 9'.

In accordance with the embodiment shown in FIG. 11, the two slots 9 and 9' do not have common connection zones or accesses and are arranged alongside each other preferably at the same height from the support base 8 or, as shown in the Figure, with the first slot 9 again arranged lower than the second slot 9'.

Figure 13:
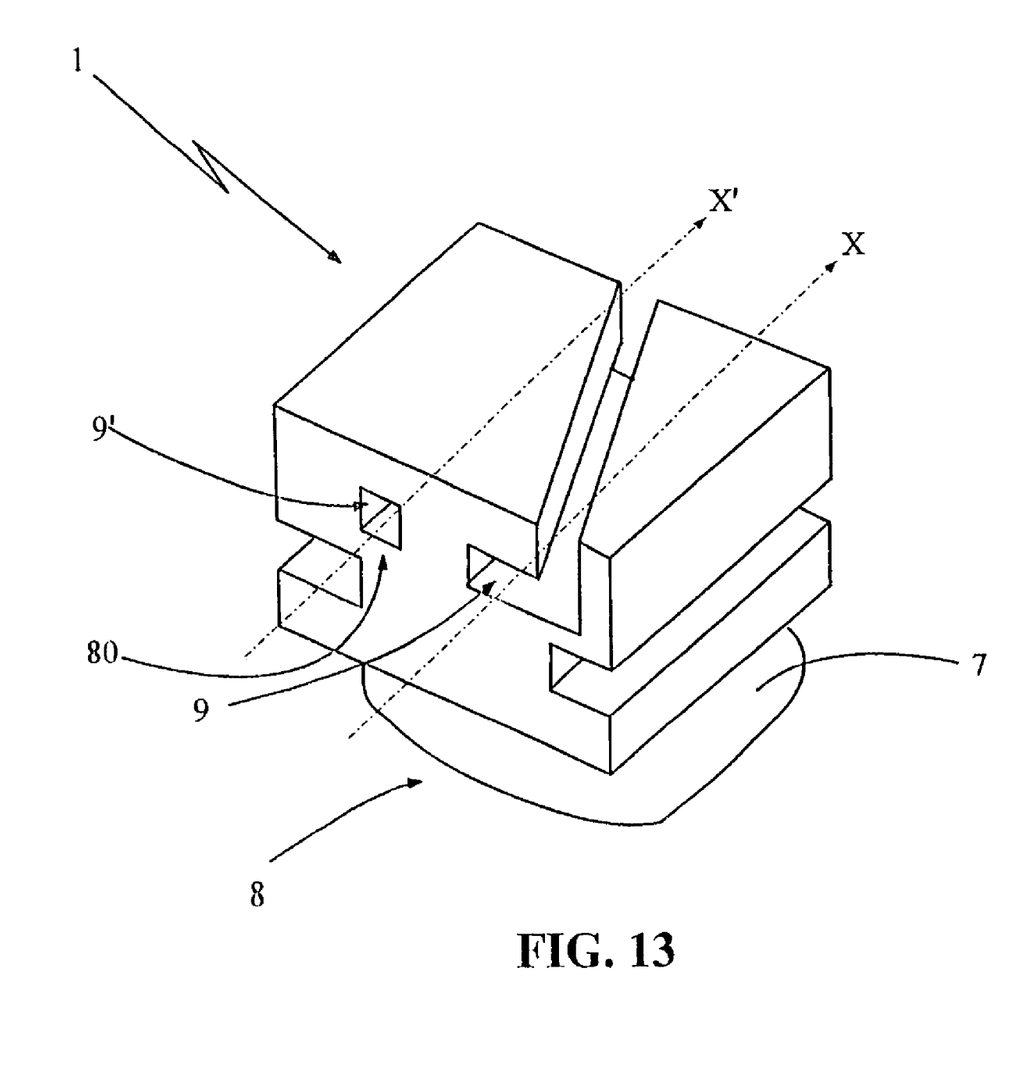
FIG. 13 shows a perspective view of a fifth embodiment of an orthodontic bracket according to the present invention envisaged in particular for a molar seat.

Differently again, in accordance with the embodiment of the bracket shown in FIG. 13 for the correction of malocciusions of molar teeth, the two slots 9 and 9' do not have common connection zones or accesses and are arranged alongside each other preferably at the same height from the support base 8. In this case the second slot 9' consists of a tube or channel inside which the wire is inserted via the inlet opening 80 situated at one of its ends.

Advantageously, the application of the superelastic wire inside the slot 9 is very practical and fast to perform since, differently from the self-ligating brackets hitherto present on the market, the bracket in question does not require movement of any element in order to allow fixing and release of the superelastic wire inside the slot 9.

In accordance with a further advantage of the present invention, the bracket is constructionally very simple to produce since it may be obtained as one piece by means of melting using the technique known as "metal injection moulding" and using the technique known as "ceramic injection moulding".

Another advantage of the bracket in question is that of ensuring firm retention of the wire whether it be of the steel type (i.e. in particular more rigid and without form memory) inserted inside the second slot 9' or of the superelastic type inserted inside the first slot 9, also in the presence of high stresses.

The present invention also relates to a method for mounting an arch wire 5 on a self-ligating orthodontic bracket 5, which is in particular but not exclusively intended to be implemented in association with the bracket 1 described above and in respect of which the same reference numbers will be maintained.

This method envisages operationally arranging firstly the self-ligating bracket 1 with the base 7 fixed in a correct position on the tooth, inserting the arch wire 5 through the opening 21 into the slot 9 and then locking it inside it so as to allow the wire 5 itself to impart a corrective action to the tooth. According to the invention, the method envisages that locking is obtained when the wire 5 passes from the access channel 20 to the slot 9. This condition is achieved for example by means of the constructional solution described above where the wire 5, when passing from the channel 20 to the slot 9, is positioned underneath the retaining portions 11 of the head pieces 13 of the lugs 10', remaining constrained underneath the bearing surfaces 19 in respect of movements in operative directions interfering with the said surfaces and indicated generically by Z in FIG. 4.

Advantageously the method thus explained is very practical and fast to implement since, differently from the self-ligating brackets present hitherto on the market, it does not require the movement of any element in order to achieve locking and unlocking of the wire inside the slot.

Superelastic form-retaining wires are available on the market, said wires being easily deformable so as to allow rapid and easy insertion thereof inside the slot and therefore being also particularly suitable for use with the bracket forming the subject of the present invention.

With the bracket design according to the present invention, it is possible to replace the type of wire used during treatment in a very easy manner, it being possible in particular to change from wires which initially and generally have round cross-sections and small dimensions with respect to the slot to wires which have increasingly larger cross-sections until the full thickness dimensions are reached with respect to the slot.

In so doing and using in particular superelastic wires, there is no longer the need to compress in a substantially constant manner the wire inside the slot by means of an elastic element and thus the substantial lack of friction of the wire inside the slot favours the sliding of the wire itself which, as is well-known, may initially be an advantage. In any case it is possible to envisage, in addition, as explained above, the use also of elastic ligatures able to exert an elastic force on the wire, or metallic ligatures.

The invention claimed is:

1. Self-ligating orthodontic bracket comprising:
 a support body (6) having a base (7) adapted to be fixed onto a tooth, a first slot defined by flat and straight walls, and an access channel (20) communicating with said first slot (9), wherein said access channel (20) is arranged crossing a receiving direction (X) in a direction (Y) slanted at an angle with respect to direction (X) so as to receive therein an arch wire (5) to impart to the tooth a corrective action when inside said first slot (9);
 a retaining element (10) adapted to engage said arch wire (5) along at least one engaging direction (Z) so as to maintain said arch wire (5) inside said slot (9);
 said retaining element (10) having at least one lug (10') formed as a unit with said support body (6) which at least partially delimits and has an inner surface facing said first slot (9), said inner surface engaging said arch wire (5) in said engaging direction (Z) by a retaining portion (11) on said inner surface of said lug (10'), said lug (10') defining said access channel (20) in a fixed angle relative to said slot;

wherein the arch wire is a form-memorizing superelastic wire introduced through said access channel by deformation to reach said slot; and wherein said arch wire is retained by the retaining portion of said lug without requiring the movement of the lug; said self-ligating orthodonic bracket in use being free of retaining ligatures.

2. A self-ligating orthodontic bracket according to claim 1, wherein said at least one lug (10') is generally mushroom shaped, said slot and said access channel define together a widened seat with a support surface comprising two separate widened zones tapering in the region of a central zone arranged so as to connect said widened zones.

3. A self-ligating orchodontic bracket according to claim 2, characterized in that said widened seat is delimited laterally by two first and by two second sides of said mushroom-shaped portions able to delimit respectively said slot and said access channel and at the top by said two retaining portions.

4. A self-ligating orthodontic bracket according no claim 1, comprising:
  a second slot arranged substantially along a receiving direction (X') adapted to receive a second arch wire;
  wherein said second arch wire is made of steel capable of imparting a corrective action to said tooth; and a renaming element in said second slot able to engage with said second wire so as to retain it inside said second slot.

5. A self-ligating orthodontic bracket according to claim 4, wherein that said first superelastic wire passes through said second slot so as to gain access to said first slot.

6. A self-ligating orthodontic bracket according to claim 4, wherein said second slot seat is situated at a height greater than said first slot in relation to said base.

7. A self-ligating orthodontic bracket according to claim 4, wherein the access of said first superelastic wire to said first slot is achieved by inserting said superelastic wire inside said second slot and then transferring it into said first slot via a connecting section situated between said first slot and said second slot.

8. A self-ligating orthodontic bracket according to claim 4, wherein the access of said first superelastic wire to said first slot is achieved by inserting said first superelastic wire inside an access channel which engages said second slot and communicates with said first slot arranged underneath said second slot.

9. A self-ligating orthodontic bracket according to claim 4, wherein said first slot and said second slot are arranged alongside each other without common connecting zones.

10. A self-ligating orthodontic bracket according to claim 9, wherein said second slot consists of a tube or channel extending through an interior of said base.

11. Self-ligating orthodontic bracket comprising:
  a support body (6) having a base (7) adapted to be fixed onto a tooth, a first slot (9) and an access channel (20) communicating with said first slot (9) in said support body (6),
  wherein said access channel (20) is arranged crossing a receiving direction (X) in a direction (Y) slanted at an angle with respect to direction (X) so as to receive therein an arch wire (5) to impart a corrective action to the tooth when inside said first slot;
  a retaining element adapted to engage said wire along at least one engaging direction (Z) substantially perpendicular to directions (X) and (Y) so as to maintain said wire inside said slot;
  said retaining element having two separate substantially mushroom-shaped lugs formed as a unit with said support body which delimit an least partially said first slot, engage said wire in said engaging direction (Z) by a retaining portion on said lugs and define said access channel in a fixed angle relative to said slot, said lugs projecting up from said support body and having two opposite faces which delimit an opening of said access channel extending substantially along a longitudinal axis in the direction Y;
  each of said mushroom-shaped lug having a head piece which extends at least partially above said slot (9), wherein said retaining portion can engage said arch wire along said engaging direction (Z);
  the receiving direction (X) of said slot defining with the longitudinal axis in the direction (Y) of said opening a fixed acute angle $\beta$ between 5 and 50°, and
  the receiving direction (X) of said slot being inside an angle $\alpha$ larger than angle $\beta$ subtended between the longitudinal axis in the direction (Y) of the opening and a direction (S) which is expected to be assumed by rotation of the slot (9) during displacement of the tooth.

* * * * *